US00PP32671P2

(12) United States Plant Patent
van Dijk

(10) Patent No.: US PP32,671 P2
(45) Date of Patent: Dec. 22, 2020

(54) ***HYDRANGEA* PLANT NAMED 'HIFIR'**

(50) Latin Name: *Hydrangea macrophylla*
Varietal Denomination: HIFIR

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 16/873,395

(22) Filed: Apr. 4, 2020

Related U.S. Application Data

(60) Provisional application No. 62/974,253, filed on Nov. 21, 2019.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

(56) References Cited

PUBLICATIONS

PLUTO UPOVROM Plant Variety Database 20200911 Citation for 'HIFIR' as per QZ PBR 20183053; Feb. 16, 2019; 1 page.*

* cited by examiner

*Primary Examiner* — Kent L Bell
(74) *Attorney, Agent, or Firm* — C. A. Whealy

(57) ABSTRACT

A new and distinct cultivar of *Hydrangea* plant named 'HIFIR', characterized by its upright and broadly spreading plant habit; freely branching habit; strong and sturdy stems; freely and continuous flowering habit; large and dense inflorescences with red to red purple-colored sterile flowers; and good post-production longevity.

2 Drawing Sheets

Figure 1:
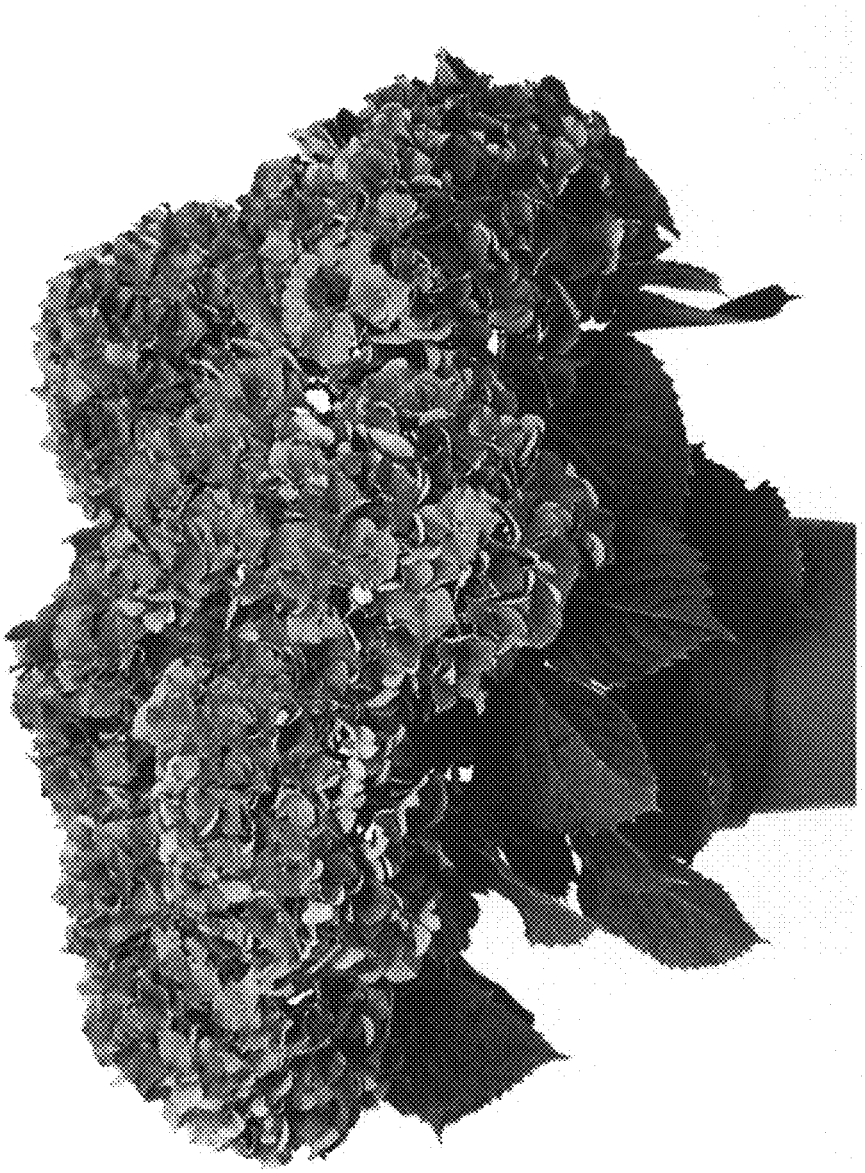

Botanical designation: *Hydrangea macrophylla.*
Cultivar denomination: 'HIFIR'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIFIR'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination in April, 2013 of two unnamed proprietary selections of *Hydrangea macrophylla*, not patented. The new *Hydrangea* plant was discovered and selected as a single flowering plant from within the progeny of the stated cross-pollination in a controlled greenhouse environment in De Lier, The Netherlands in April, 2015.

Asexual reproduction of the new *Hydrangea* plant by terminal vegetative cuttings since June, 2015 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIFIR'. These characteristics in combination distinguish 'HIFIR' as a new and distinct *Hydrangea* plant:

1. Upright and broadly spreading plant habit.
2. Freely branching habit.
3. Strong and sturdy stems.
4. Freely and continuous flowering habit.
5. Large and dense inflorescences with red to red purple-colored sterile flowers.
6. Good post-production longevity.

Plants of the new *Hydrangea* can be compared to plants of the parent selections. Plants of the new *Hydrangea* differ primarily from plants of the parent selections in the following characteristics:

1. Plants of the new *Hydrangea* are sturdier than plants of the parent selections.
2. Plants of the new *Hydrangea* have longer postproduction longevity than plants of the parent selections.

Plants of the new *Hydrangea* can also be compared to plants of *Hydrangea macrophylla* 'Hot Red', not patented. In side-by-side comparisons, plants of the new *Hydrangea* differed primarily from plants of 'Hot Red' in the following characteristics:

1. Leaves of plants of the new *Hydrangea* are darker green in color than leaves of plants of 'Hot Red'.
2. Sterile flowers of plants of the new *Hydrangea* are sturdier than sterile flowers of plants of 'Hot Red'.

3. Sepals of sterile flowers of plants of the new *Hydrangea* are more undulate than sepals of sterile flowers of plants of 'Hot Red'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'HIFIR' grown in a container.

Figure 2:
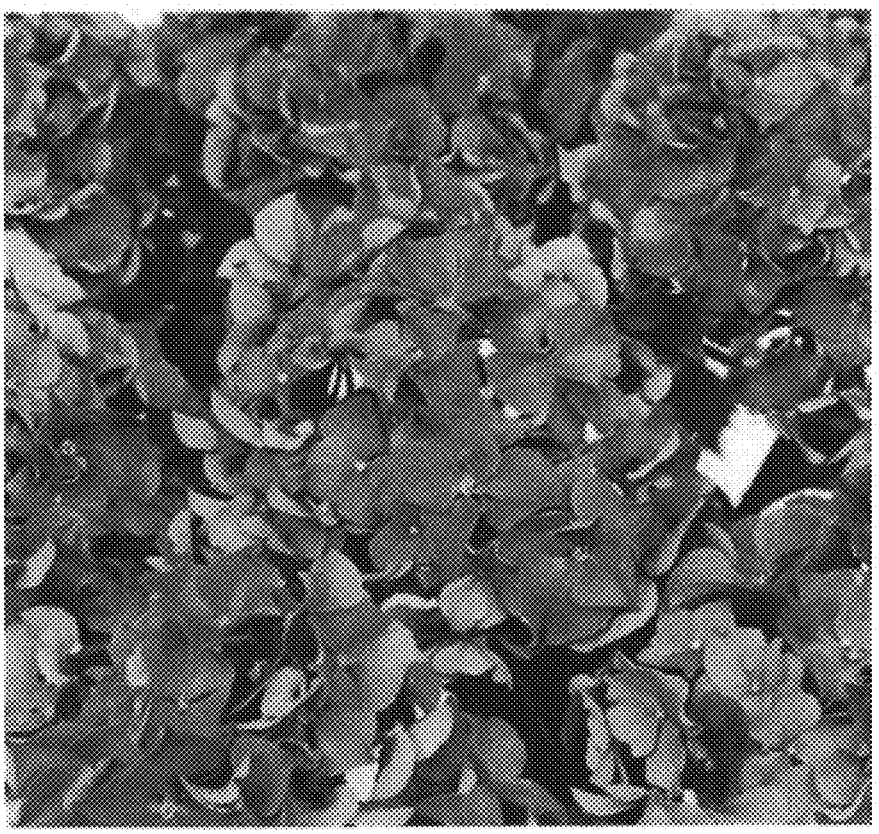

The photograph on the second sheet (FIG. 2 of 2) is a close-up view of a typical inflorescence of 'HIFIR'.

DETAILED BOTANICAL DESCRIPTION

Plants used in the aforementioned photographs and in the following description were grown during the autumn in 13-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and lightly levels were about 4,000 lux. Plants of the new *Hydrangea* were pinched one time and were two years old when the photographs and description were taken. In the following description, color references are made to The Royal Horticultural Society Colour Chart, 2015 Edition, except where general terms of ordinary dictionary significance are used. Plants are not typically "blued" (treated with aluminum sulfate).

Botanical description: *Hydrangea macrophylla* 'HIFIR'.

Parentage:

*Female, or seed, patent*.—Unnamed proprietary selection of *Hydrangea macrophylla*, not patented.

*Male, or pollen, patent*.—Unnamed proprietary selection of *Hydrangea macrophylla*, not patented.

Propagation:

*Type cutting*.—By vegetative terminal cuttings.

*Time to initiate roots, summer*.—About twelve days at temperatures about 22° C.

*Time to initiate roots, winter*.—About two weeks at temperatures about 20° C.

*Time to produce a rooted young plant, summer*.—About four weeks at temperatures about 22° C.

*Time to produce a rooted young plant, winter*.—About one month at temperatures about 19° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular in overall shape; strong and sturdy stems; moderately vigorous growth habit and moderate growth rate; about six months from propagation are required to produce a finished flowering plant.

*Plant height*.—About 29 cm.

*Plant diameter or area of spread*.—About 45.9 cm.

Lateral branch description:

*Branching habit*.—Freely branching habit with about 15 lateral branches per plant; pinching enhances lateral branch development.

*Length*.—About 13.1 cm.

*Diameter*.—About 5 mm.

*Internode length*.—About 4.6 cm.

*Strength*.—Strong, sturdy.

*Aspect*.—About 60° from vertical.

*Texture*.—Smooth, glabrous; fully developed, woody.

*Luster*.—Moderately glossy.

*Color, developing*.—Close to 144A to 144B.

*Color, fully developed*.—Close to 199B to 199C.

*Lenticels*.—Density: Sparse to medium. Length: About 1.5 mm. Width: About 0.5 mm. Color: Close to 200C.

Leaf description:

*Arrangement*.—Opposite, simple.

*Length*.—About 8.6 cm.

*Width*.—About 7 cm.

*Shape*.—Broadly ovate.

*Apex*.—Apiculate.

*Base*.—Attenuate.

*Margin*.—Coarsely serrate.

*Texture and luster, upper surface*.—Slightly rugose, glabrous; semi-glossy.

*Texture and luster, lower surface*.—Moderately rugose, glabrous; slightly glossy.

*Venation pattern*.—Pinnate.

*Color*.—Developing leaves, upper surface: Close to 143A. Developing leaves, lower surface: Close to 144A. Fully developed leaves, upper surface: Close to NN137A; venation, close to 144A. Fully developed leaves, lower surface: Close to 138A; venation, close to 146D.

*Petioles*.—Length: About 2.3 cm. Diameter: About 3.5 mm. Texture and luster, upper surface: Smooth, glabrous; slightly glossy. Texture and luster, lower surface: Smooth, glabrous; moderately glossy. Color, upper surface: Close to 144A to 144B. Color, lower surface: Close to 144B.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly and fertile flowers mostly upright.

*Fragrance*.—None detected.

*Natural flowering season*.—In the garden, plants flower continuously from the late spring to late summer in The Netherlands; flower dormancy can be broken by giving a two-month cold treatment.

*Flower longevity*.—Good postproduction longevity; sterile flowers maintain good substance for about six weeks on the plant, sterile flowers persistent; fertile flowers last about one week on the plant, fertile flowers not persistent.

*Quantity of flowers*.—Freely flowering habit; about 175 sterile flowers per panicle and about 60 fertile flowers per panicle.

*Panicle height*.—About 9.2 cm.

*Panicle diameter*.—About 14.2 cm.

*Sterile flower buds*.—Length: About 7 mm. Diameter: About 1.5 cm. Shape: Broadly cup-shaped. Color: Close to 63A; distally tinged with close to 179A.

*Fertile flower buds*.—Length: About 2.5 mm. Diameter: About 3 mm. Shape: Flattened globular. Color: Lighter than 148D tinged with close to 76B.

*Sterile flower diameter*.—About 3.6 cm.

*Sterile flower depth* (*height*).—About 9 mm.

*Fertile flower diameter*.—About 3.5 mm.

*Fertile flower depth* (*height*).—About 3 mm.

*Petals, sterile flowers*.—Quantity and arrangement: Four in a single whorl. Length: About 1.75 mm. Width: About 1.5 mm. Shape: Broadly ovate, concave. Apex: Acute. Base: Cuneate. Margin: Entire. Texture and luster, upper and lower surfaces: Smooth, glabrous; matte. Color: When opening and fully opened, upper surface: Close to 77B; towards the margins, close to 76C to 76D; color does not change with development. When opening and fully opened, lower surface: Close to 70C to 70D to lighter than 70C to 70D; color does not change with development.

*Petals, fertile flowers*.—Quantity and arrangement: Five in a single whorl. Length: About 3.5 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to N77B; towards the apex, base and margins, close to N155B; color does not change with development. When opening and fully opened, lower surface: Close to 145C tinged towards the margins with close to 70C; color does not change with development.

*Sepals, sterile flowers*.—Quantity and arrangement: Typically four, occasionally five, in a single whorl. Length: About 1.7 cm. Width: About 2 cm. Shape: Broadly rhomboidal to roughly deltoid. Apex: Abruptly acute. Base: Cuneate. Margin: Entire to slightly serrate; moderately and coarsely undulate. Texture and luster, upper and lower surfaces: Smooth, glabrous; matte. Color: When opening, upper surface: Close to 63B; distally, close to 63A to 63B. When opening, lower surface: Close to 63C. Fully opened, upper surface: Close to 53C slightly tinged with close to 58A; with development, color becoming closer to 178B strongly tinged with close to 146C. Fully opened, lower surface: Close to 63C; with development, color becoming closer to 177C to 177D tinged with close to 147C.

*Sepals, fertile flowers*.—Quantity and arrangement: Five in a single whorl. Length: About 1.5 mm. Width: About 1 mm. Shape: Ovate. Apex: Acute. Base: Broadly cuneate. Margin: Entire. Texture and luster, upper and lower surfaces: Smooth, glabrous; matte. Color: When opening, upper and lower surfaces: Close to 144C. Fully opened, upper and lower surfaces: Close to 144C; color does not change with development.

*Pedicels, sterile flowers*.—Length: About 1.7 cm. Diameter: About 1.25 mm. Strength: Moderately strong. Aspect: About 30° from peduncle. Texture and luster: Densely pubescent; matte. Color: Close to 70C.

*Pedicels, fertile flowers*.—Length: About 4 mm. Diameter: About 1 mm. Strength: Moderately strong. Aspect: About 10° from peduncle. Texture and luster: Smooth, glabrous; matte. Color: Close to 154D.

*Reproductive organs, sterile flowers*.—Stamens: Quantity per flower: Eight. Filament length: About 1 mm. Filament color: Close to 76D to lighter than 76D. Anther shape: Broadly oblong. Anther length: About 0.5 mm. Anther color: Close to 155A. Pollen amount: Scarce. Pollen color: Close to 155A. Pistils: Pistil quantity per flower: Two. Pistil length: About 1 mm. Stigma shape: Club-shaped. Stigma color: Close to 73D. Style length: About 0.5 mm. Style color: Close to 73D. Ovary color: Close to 150D.

*Reproductive organs, fertile flowers*.—Stamens: Quantity per flower: Eight. Filament length: About 1 mm. Filament color: Lighter than 145D. Anther shape: Broadly oblong. Anther length: About 0.75 mm. Anther color: Close to 150D. Pollen amount: None observed. Pistils: Pistil quantity per flower: Typically three, occasionally, two. Pistil length: About 1 mm. Stigma shape: Club-shaped. Stigma color: Close to 73D. Style length: About 0.5 mm. Style color: Close to 73D. Ovary color: Close to 150D.

*Seeds*.—To date, seed development has not been observed on plants of the new *Hydrangea*.

Pathogen & pest resistance: Under commercial production conditions, plants of the new *Hydrangea* have been observed to tolerate Powdery Mildew (*Erysiphe friesii* var. *friesii*) and *Botrytis* (*Botrytis cinerea*). Plants of the new *Hydrangea* not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIFIR' as illustrated and described.

* * * * *